United States Patent [19]

Schwartz, deceased

[11] Plant 4,513

[45] Mar. 25, 1980

[54] ROSE PLANT

[75] Inventor: Ernest Schwartz, deceased, late of Kingsville, Md., by Hazel E. Schwartz, executrix

[73] Assignee: F. Harmon Saville, Nor'East Miniature Roses, Rowley, Mass.

[21] Appl. No.: 955,379

[22] Filed: Oct. 27, 1978

[51] Int. Cl.[2] ..... A01H 5/00

[52] U.S. Cl. ..... Plt./8

[58] Field of Search ..... Plt./8

*Primary Examiner*—Robert E. Bagwill

*Attorney, Agent, or Firm*—Vincent G. Gioia

[57] ABSTRACT

A new white miniature rose of hybrid-tea shaped blooms of heavy petalage.

1 Drawing Figure

The present invention relates to a new and distinct variety of rose plant of the miniature rose class, which was originated by my crossing as seed parent the rose known as "Ma Perkins" and the rose known as "Magic Carousel" as pollen parent.

Among the novel characteristics possessed by this new variety which distinguish it from its parents and all other varieties of which I am aware are: (1) classically shaped colored blooms hybrid tea-like, long tapering bud form, (2) high centered blooms borne primarily singly to a stem in a manner typical of hybrid tea plants, (3) flowers of good petalage and very good substance, and (4) significant fragrance. Asexual reproduction by budding of the new variety as performed in Essex County, Mass., shows that the foregoing and other distinguishing characteristics come true to form and are established and transmitted through succeeding propagations.

The new and improved rose variety which I have developed is an unusually fine miniature rose producing relatively large flowers of clean white coloring, singly-borne with high center. The hybrid-tea like flower begins with classic, long tapered bud form and maintains a high center while opening while retaining good petal texture and substance. The petals reflex upon opening and roll under to form points at maturity. The plant itself is attractive in combining medium, abundant foliage with moderately branching growth.

The accompanying drawing shows typical specimens of the vegetative growth and flowers of the new variety in different stages of development and as depicted in color as nearly true as it is reasonably possible to make the same in color illustration of this character.

The following is a detailed description of my new variety, with color terminology in accordance with the Royal Horticultural Society Color Chart (RHSCC). The terminology used in color description herein refers to plate numbers in the aforementioned color chart, e.g., "155A" is plate 155A of the Royal Horticultural Society Color Chart.

Parentage: Seedling.

*Seed parent.*—"Ma Perkins".

*Pollen parent.*—"Magic Carousel".

Class: Miniature.

The following observations are made of specimens grown outdoors in Essex County, Mass., during the month of July.

1. FLOWER

Blooming habit: Recurrent.

A. *Bud.*—(1) Size: Large for miniature. (2) Form: Long, tapering. (3) Color: When sepals first divide — 155A. When petals begin to unfurl — 155B. When half-blown: 155D. Reverse side of petals — 155B. (4) Sepals: Long, thin, tapered point, shorter than mature bud; 3 of 5 sepals usually have opposed single foliation at mid point. (5) Peduncle: Length — normal. Aspect — straight, strong. Strength — erect, strong. Color — 144B.

B. *Bloom.*—(1) Size: Average size when fully expanded — about 1½ inches to 1⅞ inches. (2) Borne: Usually singly. (3) Form: High centered at first, petals reflex and become rolled under to form points at maturity. (4) Petalage: Number of petals under normal conditions — about 43 to 48. (5) Color: (during first two days) Inner petals at center of flower — 8D. Outer petals — 155A to 155B. Base of petals (point of attachment) — 5D. Reverse of petals — 155B. General tonality from a distance — rich white. (6) Color Change: As bloom ages — 155B, maintaining rich white coloring as bloom ages with color still 155B after three or more days.

C. *Petals.*—(1) Texture: Thick, good substance. (2) Appearance: Inside — soft, plushy; outside — satiny. (3) Form: Wide with short points. (4) Arrangement: Regularly arranged, shingle-like. (5) Petaloids in center: Few. (6) Persistence: Drop off cleanly. (7) Fragrance: Light and sweet. (8) Lasting quality: Moderately long lasting on plant and as cut flower.

2. REPRODUCTIVE ORGANS

A. Stamens, filaments and anthers:

(1) *Arrangement.*—Regularly arranged around styles.

(2) *Color.*—22A.

B. Pollen: Color — 22A.

C. Styles: Medium, even distribution, outer ones longer, thin.

D. Stigmas: Color — 43C.

E. Hips: None observed.

3. PLANT

A. Form: Upright, compact.

B. Growth: Vigorous, moderately branching, long cutting stems. Height attained — 15 to 18 inches under good conditions.

C. Foliage: Compound 5 to 7 leaflet leaves.

(1) *Size.*—Medium to large.

(2) *Quantity.*—Abundant, well spaced.

(3) *Color.*—New foliage: Upper side — near to 183A, under side — near to 183C. Old foliage: Upper side — 139A, under side — 137D.

(4) *Shape.*—Pointed, oval.

(5) *Texture.*—Upper side — smooth, slightly shiny. Under side — matte.

(6) *Edge.*—Serrated.

(7) *Serration.*—Regular, shallower than most miniatures.

(8) *Leaf stem.*—Color — near to 138B. Under side — 139C.

(9) *Stipules.*—Medium length, slightly bearded.

(10) *Resistance to disease.*—Blackspot — good. Mildew — good.

D. Wood:

(1) *New wood.*—Color — near to 137D. Bark — smooth.

(2) *Old wood.*—Color — near to 137D. Bark — smooth.

E. Thorns:

(1) *Thorns.*—Quantity: Few. On laterals from stalk — few. Form — long, thin, pointed, straight, slanted slightly downward. Length — medium. Color (when young) — 35C. Position — irregular.

(2) *Prickles.*—None.

F. Winter hardiness: Needs some winter protection in worst winter areas.

I claim:

1. A new and distinct variety of rose plant of the miniature class, substantially as shown and described, characterized particularly by long tapering buds opening into rich white hybrid tea-like, high centered, blooms borne primarily singly to a stem maintaining its color well upon aging.

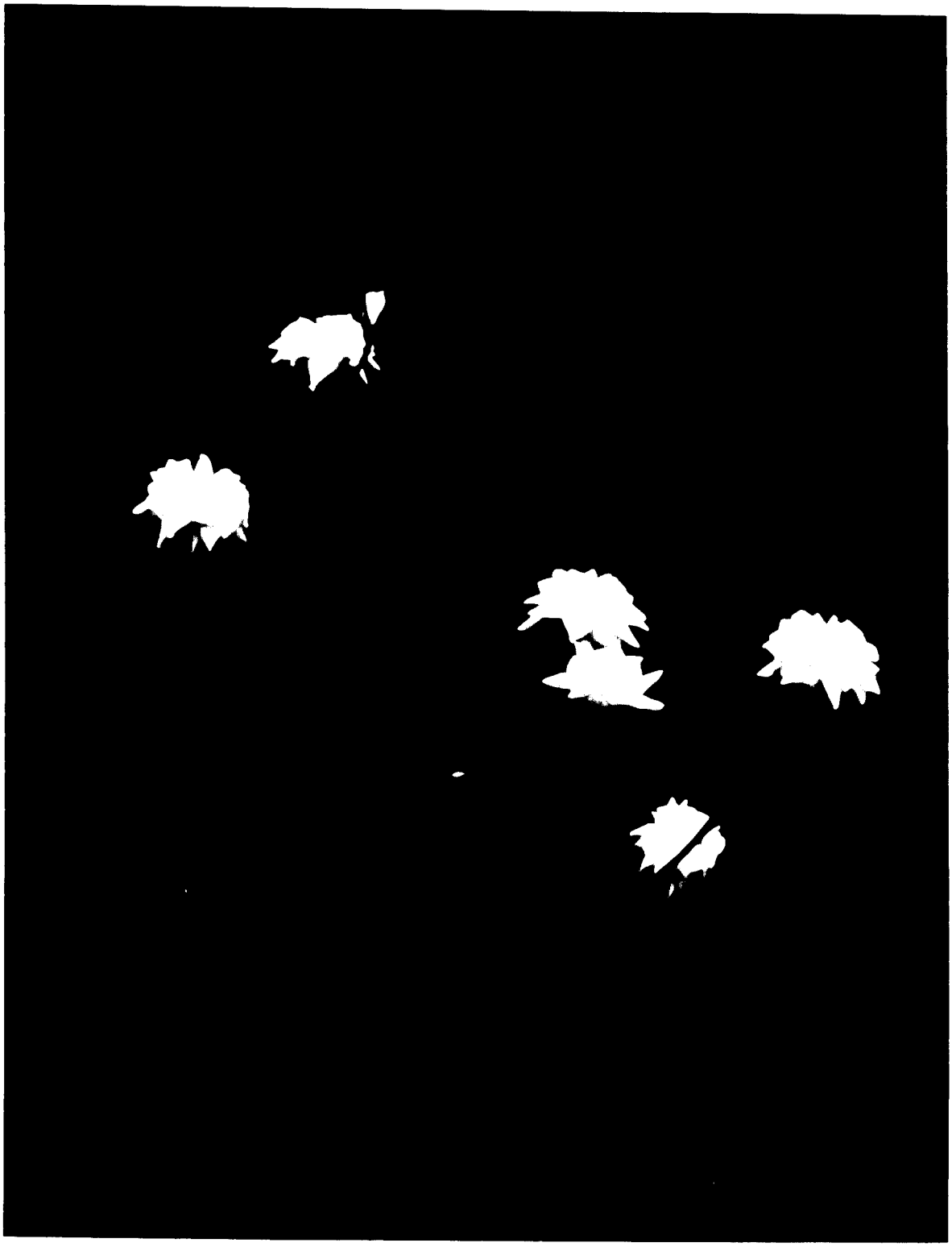

* * * * *